(12) United States Patent
Casper

(10) Patent No.: US 12,023,030 B2
(45) Date of Patent: Jul. 2, 2024

(54) TISSUE REPAIR DEVICES AND METHODS

(71) Applicant: NOVABIO TECHNOLOGIES, LLC, Lehi, UT (US)

(72) Inventor: Dolly Creger Casper, Salt Lake City, UT (US)

(73) Assignee: Novabio Technologies, LLC, Lewiston, ID (US)

(*) Notice: Subject to any disclaimer, the term of this patent is extended or adjusted under 35 U.S.C. 154(b) by 428 days.

(21) Appl. No.: 17/465,464

(22) Filed: Sep. 2, 2021

(65) Prior Publication Data
US 2022/0054133 A1 Feb. 24, 2022

Related U.S. Application Data

(62) Division of application No. 13/796,607, filed on Mar. 12, 2013, now abandoned.
(Continued)

(51) Int. Cl.
*A61B 17/08* (2006.01)
*A61B 17/122* (2006.01)

(52) U.S. Cl.
CPC ........ *A61B 17/083* (2013.01); *A61B 17/1227* (2013.01)

(58) Field of Classification Search
CPC ..... A61B 17/064; A61B 17/083; A61B 17/11; A61B 17/1114; A61B 17/1128;
(Continued)

(56) References Cited

U.S. PATENT DOCUMENTS 4,204,541 A * 5/1980 Kapitanov ........... A61B 17/064
606/221
4,300,244 A 11/1981 Bokros
(Continued)

FOREIGN PATENT DOCUMENTS

EP 2832319 2/2015
JP 2004073221 A 3/2004
(Continued)

OTHER PUBLICATIONS

European Search Report dated Jul. 12, 2016 for EP application 13863287.
(Continued)

*Primary Examiner* — Ryan J. Severson
(74) *Attorney, Agent, or Firm* — Foley & Lardner LLP

(57) ABSTRACT

Devices and methods for reconnecting or supporting torn, damaged or weak tissue are disclosed. The disclosed embodiments can be used on long slender tissue such as ligaments, tendons, nerves, vessels, intestines, muscles, bones, appendages and any other elongate tissue within the body, of both humans and other animals. The devices can wrap around elongate tissue and is capable of supporting the tissue or keeping two severed ends in close proximity to one another. The devices can be used in addition to or in lieu of sutures. The devices can function similar to a Chinese Finger Trap and are capable of decreasing in diameter upon extension, thus constricting upon the tissue. The multiple coils of the devices can make sufficient surface contact on the ligament or tendon, using friction to keep the device in place, while also allowing access for diffusion of oxygen and nutrients.

17 Claims, 18 Drawing Sheets

Related U.S. Application Data

(60) Provisional application No. 61/736,000, filed on Dec. 11, 2012.

(58) Field of Classification Search
CPC ............ A61B 17/1146; A61B 17/1227; A61B 2017/00526; A61B 2017/0649; A61B 2017/1103; A61B 2017/1107; A61B 2017/1132; A61F 2/0811
See application file for complete search history.

(56) References Cited

U.S. PATENT DOCUMENTS

| | | | |
|---|---|---|---|
| 4,512,338 A | 4/1985 | Balko et al. | |
| 4,881,939 A * | 11/1989 | Newman | A61B 17/12009 128/DIG. 25 |
| 5,191,903 A | 3/1993 | Donohue | |
| 5,556,428 A * | 9/1996 | Shah | A61B 17/1146 606/151 |
| 5,583,319 A | 12/1996 | Lieurance | |
| 5,972,001 A * | 10/1999 | Yoon | A61B 17/1227 606/139 |
| 5,984,896 A | 11/1999 | Boyd et al. | |
| 6,063,111 A | 5/2000 | Hieshima et al. | |
| 6,171,320 B1 | 1/2001 | Monassevitch | |
| 6,171,338 B1 | 1/2001 | Talja et al. | |
| 6,174,333 B1 | 1/2001 | Kadiyala et al. | |
| 6,485,503 B2 * | 11/2002 | Jacobs | A61B 17/08 606/151 |
| 6,648,911 B1 * | 11/2003 | Sirhan | A61B 17/12 623/1.15 |
| 6,984,241 B2 * | 1/2006 | Lubbers | A61B 17/0487 606/103 |
| 7,344,558 B2 * | 3/2008 | Lorenzo | A61B 17/1214 623/1.11 |
| 7,611,521 B2 * | 11/2009 | Lubbers | A61B 17/685 81/436 |
| 8,556,930 B2 * | 10/2013 | Ellingwood | A61B 17/0057 606/139 |
| 8,833,130 B2 * | 9/2014 | Matsunaga | A61B 17/1114 140/71 C |
| 9,427,309 B2 * | 8/2016 | Kubiak | A61B 17/0487 |
| 11,123,177 B2 * | 9/2021 | Valavanis | A61F 2/0811 |
| 2001/0044637 A1 * | 11/2001 | Jacobs | A61B 17/08 606/221 |
| 2002/0010481 A1 | 1/2002 | Jayaraman | |
| 2003/0040790 A1 | 2/2003 | Furst | |
| 2003/0040803 A1 | 2/2003 | Rioux et al. | |
| 2003/0114920 A1 | 6/2003 | Caro et al. | |
| 2003/0195562 A1 | 10/2003 | Collier et al. | |
| 2004/0193217 A1 * | 9/2004 | Lubbers | A61B 17/683 606/232 |
| 2004/0260384 A1 | 12/2004 | Allen | |
| 2006/0095058 A1 | 5/2006 | Sivan et al. | |
| 2006/0142845 A1 | 6/2006 | Molaei et al. | |
| 2006/0212047 A1 | 9/2006 | Abbott et al. | |
| 2007/0056591 A1 | 3/2007 | McSwain | |
| 2007/0203519 A1 | 8/2007 | Lorenzo et al. | |
| 2008/0004640 A1 * | 1/2008 | Ellingwood | A61B 17/0057 606/151 |
| 2008/0228146 A1 | 9/2008 | Shaked et al. | |
| 2009/0132031 A1 | 5/2009 | Cook et al. | |
| 2009/0142132 A1 | 6/2009 | Klein | |
| 2009/0157168 A1 | 6/2009 | Degen | |
| 2009/0248142 A1 | 10/2009 | Perkins et al. | |
| 2010/0010293 A1 | 1/2010 | Sato et al. | |
| 2010/0010514 A1 * | 1/2010 | Ishioka | A61B 17/11 606/151 |
| 2010/0010520 A1 | 1/2010 | Takahashi et al. | |
| 2010/0168841 A1 | 7/2010 | Furst et al. | |
| 2010/0292785 A1 | 11/2010 | Seguin et al. | |
| 2011/0276071 A1 | 11/2011 | Connor et al. | |
| 2012/0083820 A1 | 4/2012 | Carman et al. | |
| 2012/0215236 A1 * | 8/2012 | Matsunaga | B21F 3/04 606/151 |
| 2012/0226296 A1 | 9/2012 | Bindra et al. | |
| 2013/0013065 A1 | 1/2013 | Bills | |
| 2013/0103166 A1 | 4/2013 | Butler et al. | |
| 2014/0163586 A1 | 6/2014 | Holt | |
| 2022/0054133 A1 * | 2/2022 | Holt | A61B 17/083 |

FOREIGN PATENT DOCUMENTS

| | | |
|---|---|---|
| JP | 2009039139 A | 2/2009 |
| WO | 2002039906 | 5/2002 |
| WO | 2006072926 | 7/2006 |
| WO | 2011091169 A1 | 7/2011 |

OTHER PUBLICATIONS

Core Essence Orthopedics, Inc., "Pontis Endotendonous Repair System", 2011 Core Essence Orthopedics, Inc.

Diraimo Jr., et al., "Distal Biceps Tendon Repair Using the Toggle Loc with Zip Loop", Orthopedics, Dec. 2008, vol. 31, No. 12, pp. 1201-1204.

Su, et al., "Device for Zone-II Flexor Tendon Repari", The Journal of Bone and Joint Surgery, JBJS.Org, vol. 87-A, No. 5, May 2005.

Tantadprasert, et al., "A Biomechanical Comparison of a Tendon Repair Device and 4 Stranded, Cruciate Repair Sutures for Flexor Tendon Ruptured", J Med Assoc Thai vol. 92, No. 11, 2009.

* cited by examiner

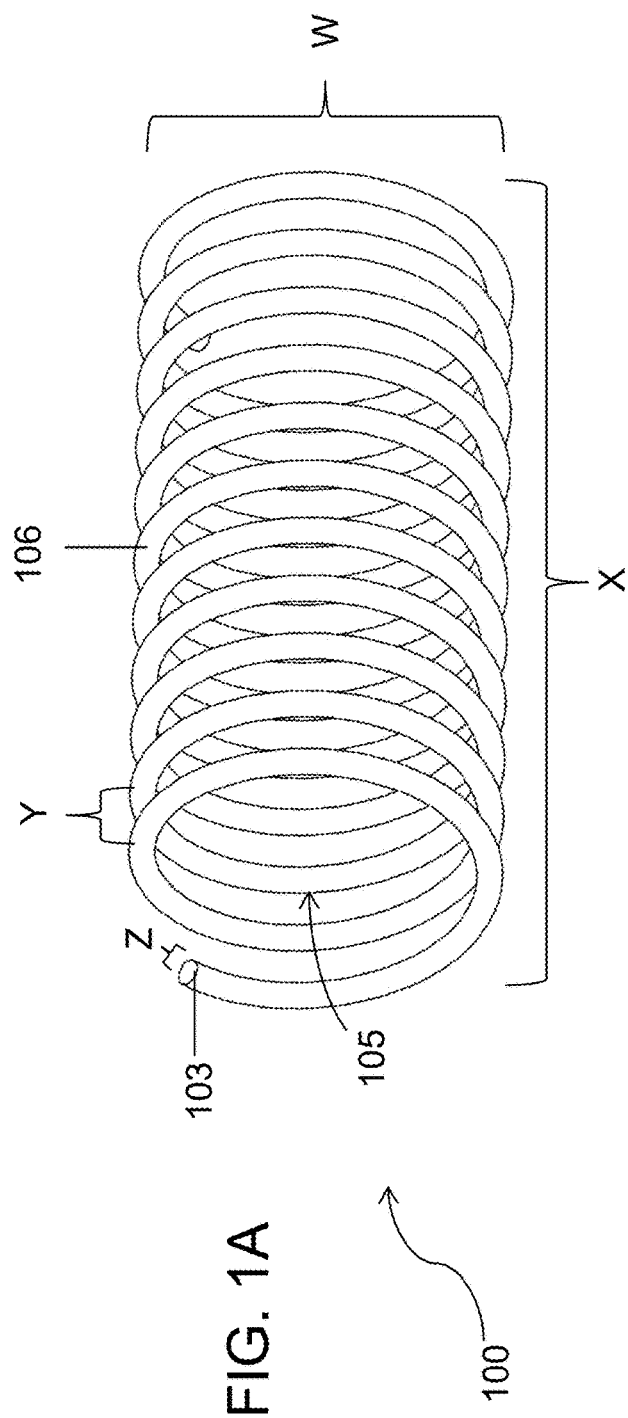
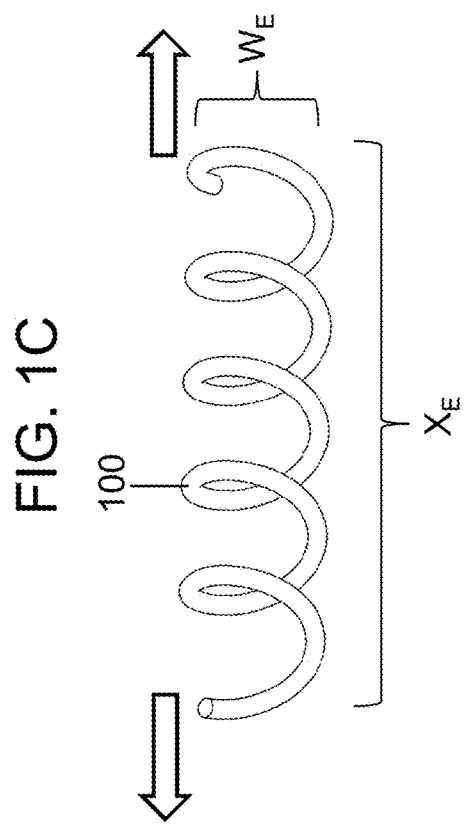
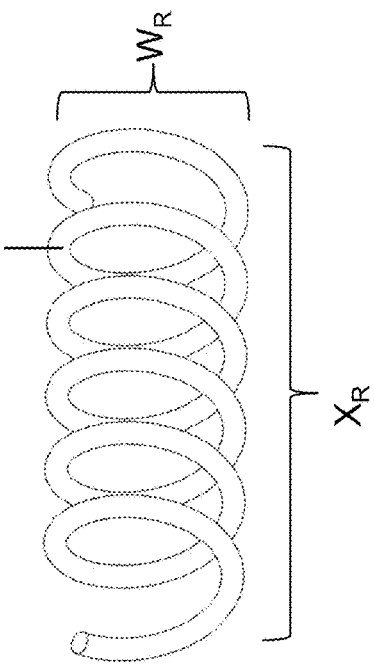

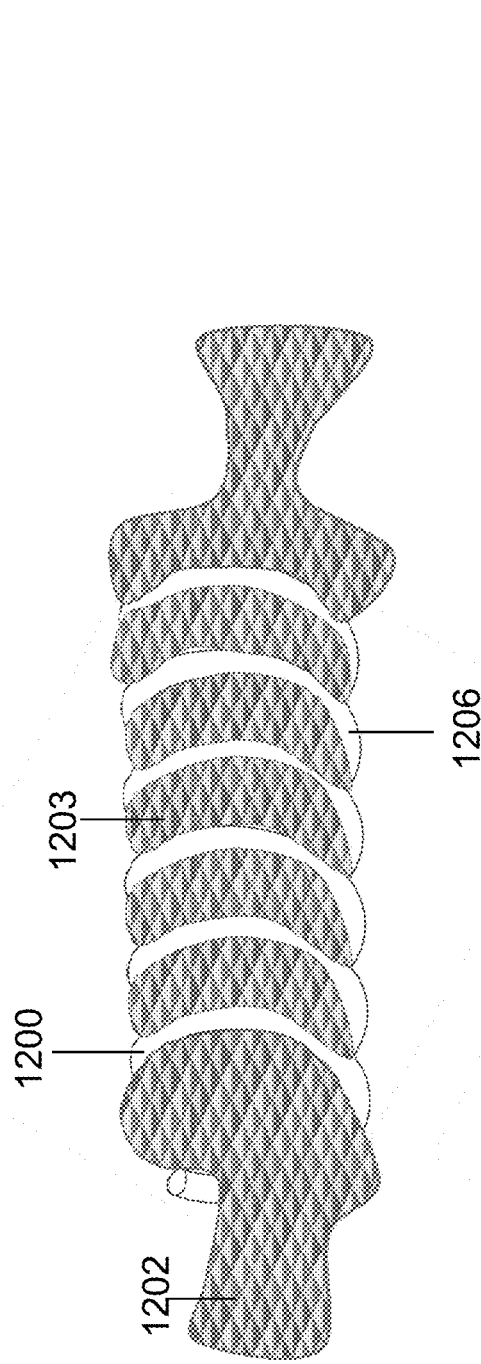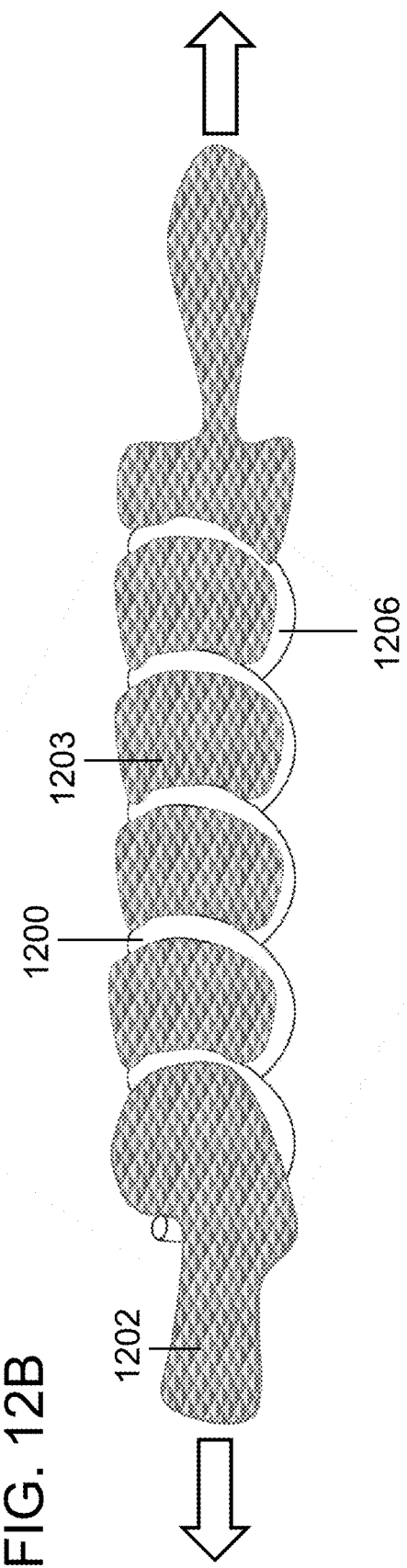
FIG. 12A
FIG. 12B

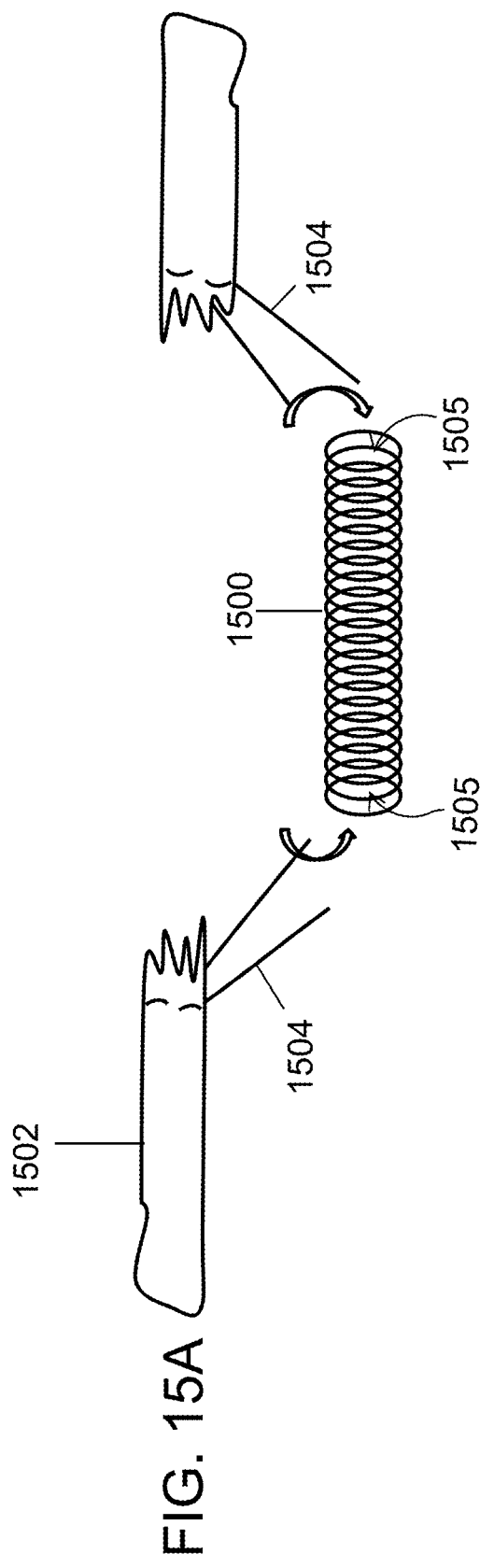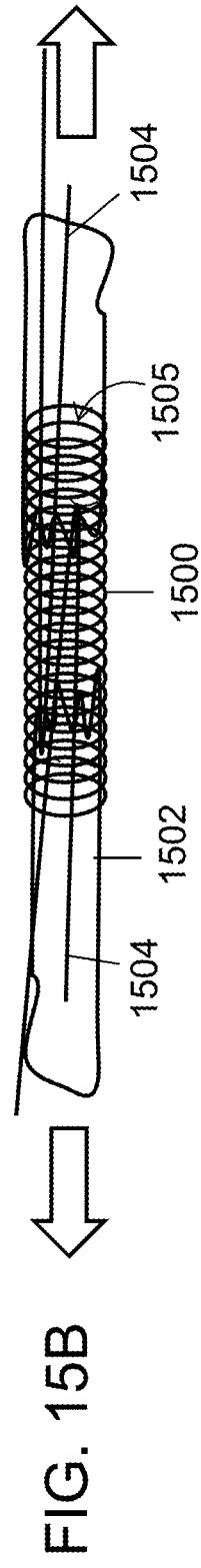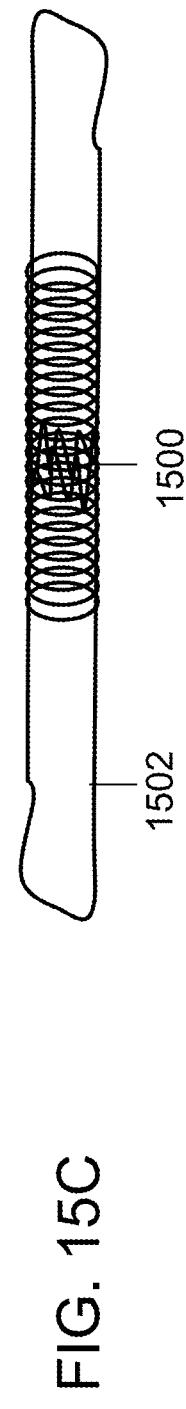

TISSUE REPAIR DEVICES AND METHODS

RELATED APPLICATIONS

The present application is a divisional application of U.S. patent application Ser. No. 13/796,607, filed, Mar. 12, 2013, and entitled "TISSUE REPAIR DEVICES AND METHODS" which claims benefit of priority under 35 U.S.C. § 119(e) of U.S. Provisional Patent Application No. 61/736,000, filed Dec. 11, 2012, and entitled "RECOMBINATION AND SUPPORT DEVICES AND METHODS FOR INJURED TISSUE", both of which are hereby incorporated herein by refence in their entirety.

TECHNICAL FIELD

This disclosure relates generally to the field of surgery. More particularly it relates to devices and methods to support weak tissue or for moving two regions of tissue towards each other to reconnect or support tissue that is separated or at risk of separation.

BRIEF DESCRIPTION OF THE DRAWINGS

The written disclosure herein describes illustrative embodiments that are non-limiting and non-exhaustive. Reference is made to certain such illustrative embodiments that are depicted in the figures, in which:

FIG. 1A is a perspective view of a tissue repair device, according to one embodiment of the present disclosure.

FIG. 1B is a side view of a tissue repair device, according to one embodiment, in a relaxed state.

FIG. 1C is a side view of a tissue repair device, according to one embodiment, in an extended state and having a decreased coil diameter upon extension.

FIG. 12A is a side view of a tissue repair device encircling and engaged with an elongate tissue.

FIG. 12B is a side view of the tissue repair device of FIG. 12A in an extended state engaging the elongate tissue is it is extended.

FIG. 15A illustrates a method of connecting sutures to either end of a severed elongate tissue and threading the sutures through a tissue repair device.

FIG. 15B illustrates the injured elongate tissue pulled through the tissue repair device of FIG. 15A using the sutures.

FIG. 15C illustrates the injured tissue in place within the tissue repair device of FIG. 15A.

Figure 2:
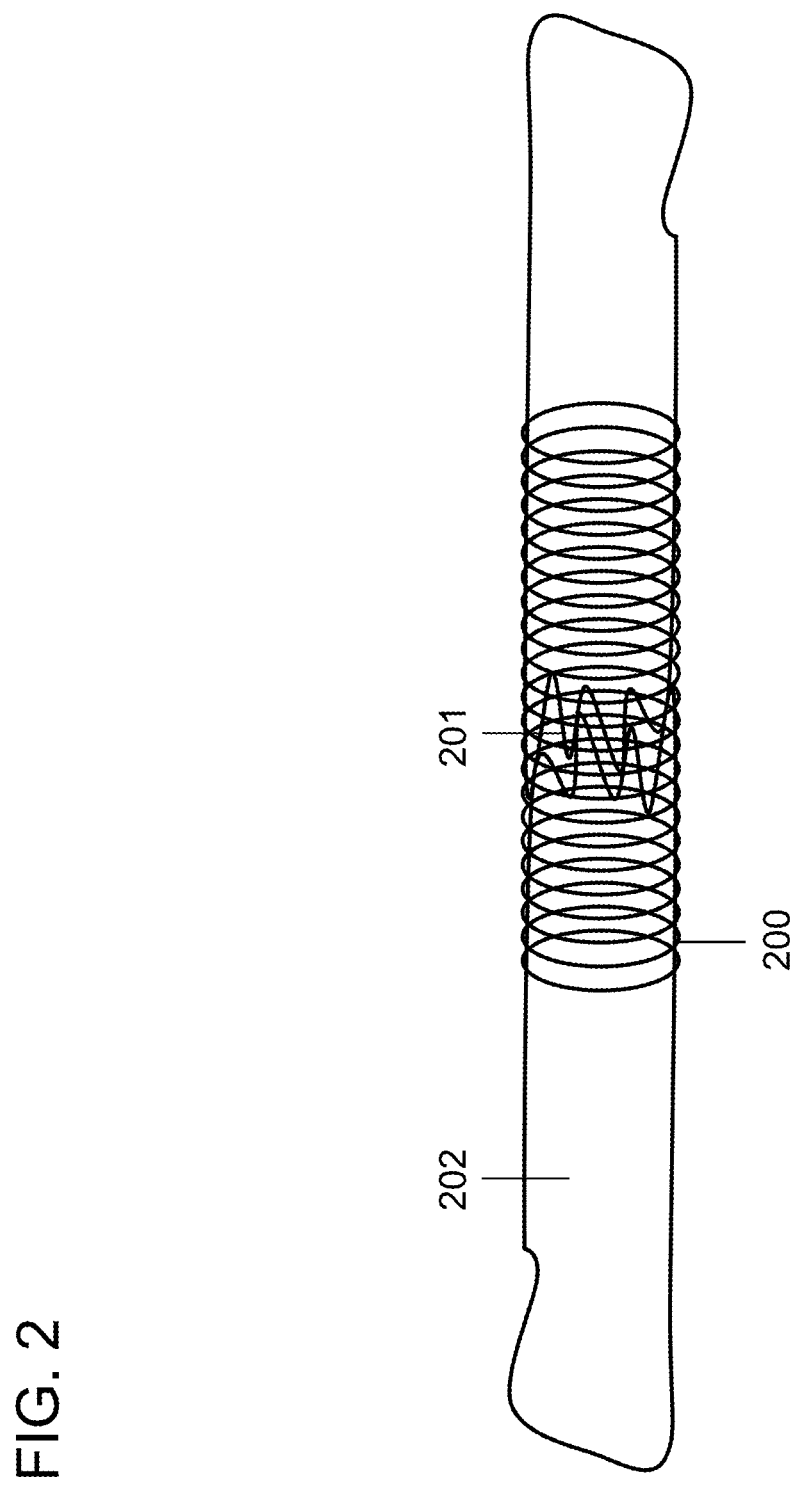
FIG. 2 is a side view of a tissue repair device, according to one embodiment, encircling severed or injured tissue.

Other features of the present embodiments will be apparent from the accompanying drawings and from the detailed description that follows.

DETAILED DESCRIPTION

Soft tissue injuries such as lacerations of ligaments and tendons can be repaired using sutures. However, when the tissue is under stress such as tensile stress, high tension can result at discrete suture sites and cause sutures to tear through the tissue. Torn tissue can require a repeat surgery to be repaired. The disclosed tissue repair devices can be used to effectively ligate and/or support torn or otherwise damaged tissue. The disclosed tissue repair devices distribute tension along repaired tissue and thus decrease the risk of injured tissue being torn after repair.

Soft tissue tears, such as tears of the Patellar and Achilles tendon rupture, can result in "mop ends" or frayed edges at the torn ends. These frayed ends can be time consuming and difficult to suture together, particularly in a manner to promote healing of the tear. The disclosed tissue repair devices can gather frayed mop ends and promote healing.

The disclosed tissue repair devices and methods can also be used to connect or support other elongate tissue within the body such as nerves and blood vessels. Sutures injure tissue in order to remain fixed in place. The disclosed tissue repair devices and methods of treatment can connect or support weak, damaged, or severed tissue while causing minimal or no damage to the tissue.

The present disclosure provides tissue repair devices for recombining, reconnecting and/or supporting torn, damaged or weak tissue. Specifically the disclosed devices can be used on elongate, slender tissue such as ligaments, tendons, nerves, vessels, intestines, muscles, bones, appendages and any other elongate tissue within the body. The devices can be used in both humans and animals. The present disclosure also provides methods for recombining, reconnecting or supporting torn, damaged or weak tissue, including administering the disclosed devices onto damaged tissue. The present disclosure also provides manufacturing processes for the creation of a device to reconnect damaged tissue.

The disclosed embodiments offer improved distribution of tension compared to sutures to prevent tissue from tearing under stress.

The disclosed embodiments do not need to pierce the tissue to remain in place.

The disclosed embodiments may reconnect or support tissue that is separated or at risk of separation.

In accordance with the principles of the present disclosure, the disclosed embodiments decrease tension at the wound site by distributing tension along the device and alleviating direct tension on the tissue.

The disclosed embodiments can encircle and engage or grip elongate tissue, using principles of friction and constriction, without causing damage to the tissue, for example, to support the damaged elongate tissue and/or to maintain two separated ends of the elongate tissue in close proximity to one another. The disclosed embodiments can provide mechanical support, stability, and the introduction of biologics such as proteins, cells, and growth factors to injured tissue. The disclosed embodiments may facilitate healing by allowing nutrients and oxygen to diffuse into the tissue through the gaps in the coils. For example, the disclosed embodiments may be porous, drug-eluting, and/or otherwise enhanced to promote tissue regeneration and cellular growth of the damaged tissue.

The disclosed embodiments may facilitate early mobilization of the injured tissue by stretching and moving with the tissue. The disclosed embodiments may reduce time to repair torn and injured tissue, compared to suturing and other methods. The disclosed embodiments may be used in conjunction with or in place of sutures.

The disclosed embodiments can be connected directly to soft tissue, and may not involve mounting to, for example bone, thus, limiting or even preventing any damage to the bone growth plate. The disclosed embodiments may enable tendons or ligaments that become frayed and swollen to be enclosed within a coil to more easily slide within the tight sheath. The disclosed embodiments may also facilitate manipulation of the severed tendon through the sheath during surgery.

One embodiment may be connected to soft tissue at a first end and bone at a second end to reduce tension at the soft tissue-bone interface.

The disclosed embodiments can encapsulate frayed mop ends of a ligament or tendon, thus reducing the need for complex suturing and decreasing risk of scar adhesion within the tissue sheath.

The disclosed embodiments can constrict upon a suture site so that the tendons can glide more readily within the sheath.

The disclosed embodiments may allow soft tissue to press up or outward between the coils, creating multiple catch points to inhibit or even prevent the tissue from slipping within the coil.

The disclosed embodiments may decrease in diameter upon extension, constricting on the elongate tissue and remaining in place even during extension. In particular, a lumen through the device may decrease in diameter upon extension. This decrease in diameter upon extension, can accommodate the decrease in diameter of elongate tissue that may occur when the elongate tissue is extended, thus allowing the device to maintain proper contact and engagement during extension and relaxation of the elongate tissue. The disclosed embodiments may employ principles of friction and constriction to remain in place and maintain contact with injured tissue.

The disclosed embodiments may increase in diameter during relaxed states, allowing for the least constriction and maximum diffusion of nutrients to the damaged tissue within the device.

The disclosed embodiments can be made of biodegradable polymers that can be broken down by the body after the injured tissue is sufficiently healed, allowing the native tissue to return to its normal state. Examples of polymers and constituents of co-polymers that can be used are polycaprolactone, polyurethane, polylactic acid, polyglycolic acid, polyvinyl alcohol, polyvinylpyrrolidone, polyester, and poly(hydroxyalkanoate).

The disclosed embodiments can be made of naturally biodegradeable materials that can be broken down by the body after the injured tissue is healed, allowing the native tissue to return to its normal state. Examples of natural materials that can be used are extracellular matrix proteins such as collagen, fibronectin, fibrinogen, lamanin, elastin, keratin and polysaccharides, such as starch, cellulose, and chitosan.

The disclosed embodiments can also be infused with, or otherwise include nutrients, supplements, medicaments, sugars, growth factors, proteins, and/or hormones, which may promote and enhance healing of the elongate tissue. For example, as the biodegredable polymers and/or natural materials may include elements to promote tissue growth and/or healing that may be released as the biodegradeable polymers and/or natural materials are broken down by the body.

The disclosed embodiments can be made of non-biodegradable polymers that will remain in place to continue to support the injured tissue. Examples of polymers and constituents of co-polymers that can be used are polytetrafluoroethylene, polyurethane, polystyrene, polycarbonate, polyester, polysulfone, polyethylene terephthalate, polyethylene, polypropylene, polyurethane, silicone, polydimethylsiloxane, polymethylmethacrylate, and polyhydroxyethyl methacrylate, and polyetheretherketone.

The disclosed embodiments can be made of metals or metal alloys that will remain in place to continue to support the injured tissue. Examples of metals or constituents of metal alloys that can be used include nitinol, stainless steel, cobalt, chromium, titanium, platinum, iridium, tungsten, tantalum, aluminum, vanadium, molybdenum, silver, copper, silicon, and tin.

The disclosed embodiments can be made of metals or metal alloys that can degrade. Examples of metals or components in metal alloys that can be used include iron, magnesium, silicon, cobalt, tungsten, boron, carbon, lead, and sulfur.

The disclosed embodiments can be made of a ceramic that can be degradable or non-degradable. Examples of ceramics include hydroxyapetite, bioglass, calcium phosphate, titanium nitride, tungsten carbide, titanium carbon nitride, aluminas, $SiO_2$, $Na_2O$, $CaO$, $P_2O_5$ and zirconia.

The disclosed embodiments may include deployment during surgery by positioning the open end of the coil at one of the ends onto the tissue and twisting the coil onto the tissue much like twisting a key ring onto a key.

The disclosed embodiments may involve twisting the coil onto the ligament or tendon, which may allow the device to be deployed at a site of a partial tear and complete tear of the injured elongate tissue.

The disclosed embodiments may include deployment during surgery by suturing each end of the severed tissue and using the sutures to pull the tissue into the lumen of the coiled device.

The disclosed embodiments may include deployment by reversing the coil of the device to increase the diameter of the coil to more easily allow insertion of wounded tissue.

The presently disclosed embodiments of devices may be created using injection molding processes.

The presently disclosed embodiments of devices can be created by wrapping extruded polymer around a dowel.

The presently disclosed embodiments of devices can be created by wrapping metal around a dowel.

Certain embodiments of the present disclosure will now be discussed with reference to the accompanying drawings and reference numerals provided therein so as to enable one skilled in the art to practice the present invention. The drawings and descriptions are examples of various aspects of the invention and are not intended to narrow the scope of the claims to the inventions. Also, for the sake of simplicity, the illustrated devices and tissue may be represented as cylindrical in shape, however each of these embodiments can be altered to accommodate a device and tissue shape that is not cylindrical.

FIG. 1A is a perspective view of a tissue repair device 100, according to one embodiment. The tissue repair device 100 comprises a coil or spiral shape formed by a coil member 103 arranged in a coil or spiral to form a plurality of interconnected turns 106 that creates a lumen 105 at its center. The tissue repair device 100 can have a length of X and spacing of Y between the turns 106 of the coil 105 of the device 100. The spacing Y between the turns 106 can vary along the length X of the tissue repair device 100. The coil member 103 has a thickness Z, which can vary along the length X of the device 100. A diameter W of the turns 106 of the coil member 103 can be varied along the length X of the device 100, which correspondingly varies the diameter of the lumen 105. FIG. 1B shows a tissue repair device 100, according to one embodiment, in a relaxed state in which the coil has a first (relaxed) coil diameter $W_R$ and a first relaxed length $X_R$. FIG. 1C shows the tissue repair device 100 of FIG. 1B in an extended state and illustrates a resultant decrease in coil diameter W, to a second (extended) coil diameter $W_E$ and an extended length $X_E$, as seen compared to the relaxed coil diameter $W_R$ and relaxed coil length $X_R$. The tissue repair device 100 may approximate or function in a manner similar to a "Chinese finger trap" in concept by reducing in diameter upon extension, allowing the device to accommodate any decrease in diameter seen in the elongate tissue such as a ligament or tendon during extension.

The coil member 103 may be formed of a biodegradable polymers and/or natural materials that can be broken down by the body after the injured tissue is sufficiently healed, allowing the native tissue to return to its normal state. Examples of polymers and constituents of co-polymers that can be used are polycaprolactone, polyurethane, polylactic acid, polyglycolic acid, polyvinyl alcohol, polyvinylpyrrolidone, polyester, and poly(hydroxyalkanoate). Examples of natural materials that can be used are extracellular matrix proteins such as collagen, fibronectin, fibrinogen, lamanin, elastin, keratin and polysaccharides, such as starch, cellulose, and chitosan.

The coil member 103 can be infused with, or otherwise include nutrients, supplements, medicaments, sugars, growth factors, proteins, and/or hormones, which may promote and enhance healing of the elongate tissue. For example, as the biodegredable polymers and/or natural materials may include elements to promote tissue growth and/or healing that may be released as the biodegradeable polymers and/or natural materials are broken down by the body.

Portions (or all) of the coil member 103 may be porous. The porosity of the coil member 103 may promote tissue growth and/or cellular in-growth, which may enhance engagement or securement of the tissue repair device 100 relative to the injured tissue and/or surrounding tissue. Porosity of the coil member may also contribute to coil compliance and degradation rate. As will be described below, coating may be employed to enhance or reduce porosity of the coil member 103.

FIG. 2 shows a tissue repair device 200 encircling an injured portion 201 of an elongate tissue 202. The tissue repair device 200 may employ principles of friction and constriction to maintain engagement with and secure the injured portion 201 of the elongate tissue 202 in place, and to limit slipping of the device 200 along the tissue 202. The tissue repair device 200 may employ principles of friction and/or constriction to remain fixed in place relative to the elongate tissue 202. For example, sutures may not be needed to maintain the device 200 in a fixed position relative to the elongate tissue 200.

Figure 3:
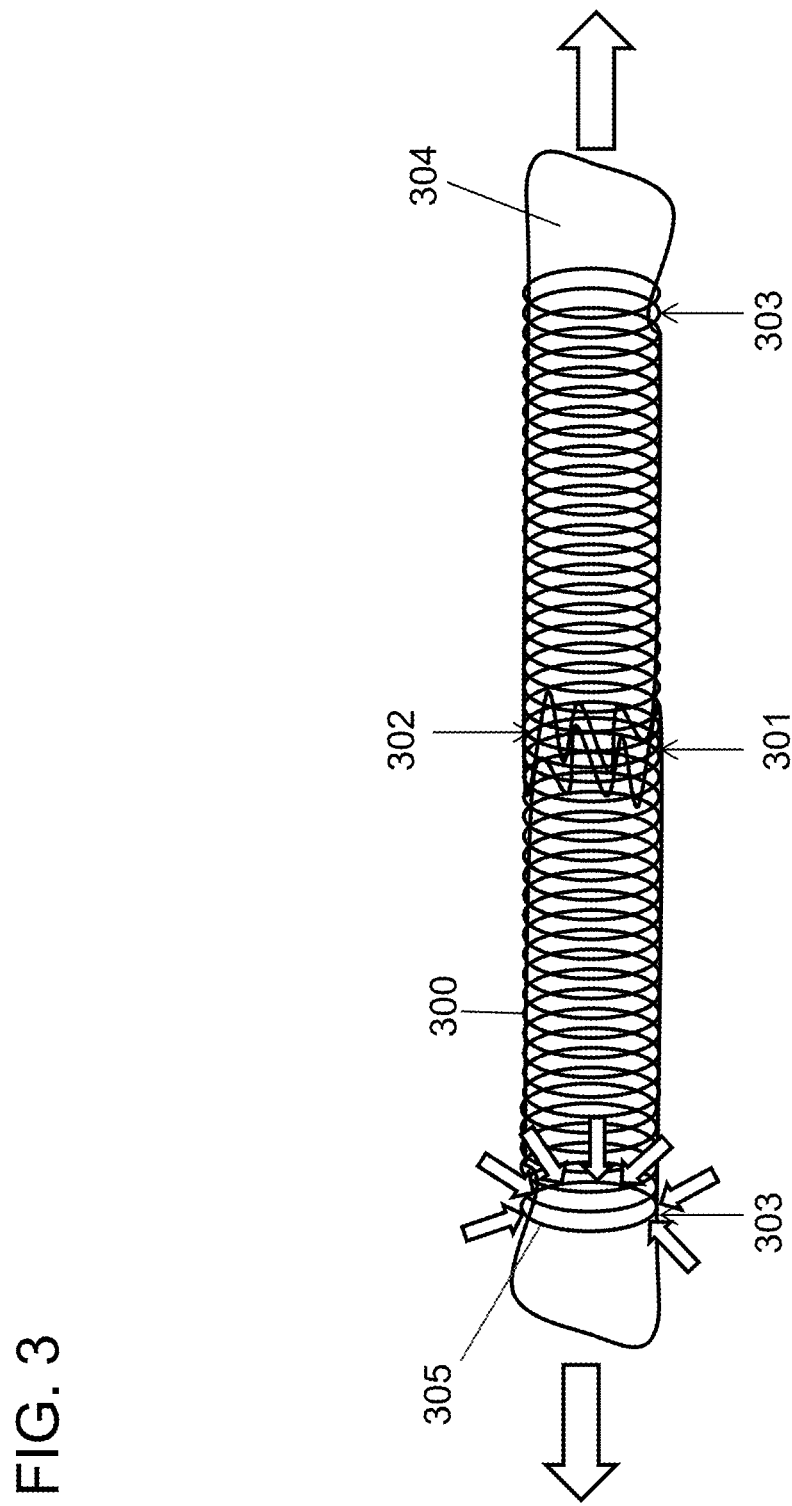
FIG. 3 is illustrates tension distribution within a tissue repair device during extension, in which tension is distributed circumferentially and alleviates tension at the wounded site of the tissue.

FIG. 3 shows a tissue repair device 300, according to one embodiment. The tissue repair device 300 is shown encapsulating injured tissue 304. The tension of the tissue repair device 300 during extension is equally distributed circumferentially 305 around the device, resulting in constriction of the tissue repair device 300 to engage or grip the elongate tissue. This circumferential tension distribution reduces the risk of tearing tissue that is in contact with the device 300, particularly compared to sutures having tension highly concentrated at a single site of insertion. The tension in the device 300 (and corresponding constriction of the device 300) may be less toward the outside ends 303 and greater at the center 301 of the device 300. The increased tension at the center of the device 301 alleviates the tension experienced by the injured tissue 304 at its center 302, reducing the risk of tissue separation and/or tearing of sutures at the injured site. The illustrated tissue repair device 300 may be used in conjunction or in lieu of sutures to connect together injured tissue, such as free (or separated) ends of torn (or partially torn) elongate tissue.

Figure 4:
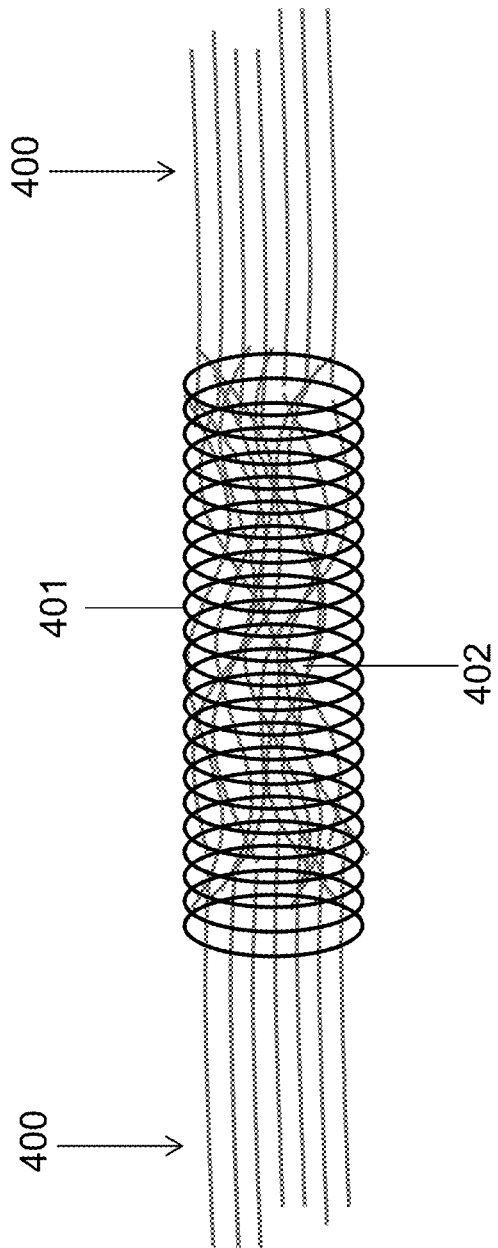
FIG. 4 illustrates a side view of a tissue repair device, according to one embodiment, encapsulating frayed tissue.

FIG. 4 shows a tissue repair device 401 enclosing or encircling frayed ends 402 of an elongate tissue 400 circumferentially. The illustrated tissue repair device 401 can gather frayed ends 402 by encapsulation, removing a need for complex suturing to gather the frayed ends. The frayed ends 402 are gathered within a lumen of the tissue repair device. The tissue repair device 401 may maintain the frayed ends 402 in close proximity to one another to facilitate and enhance healing of the elongate tissue 400.

Figure 5:
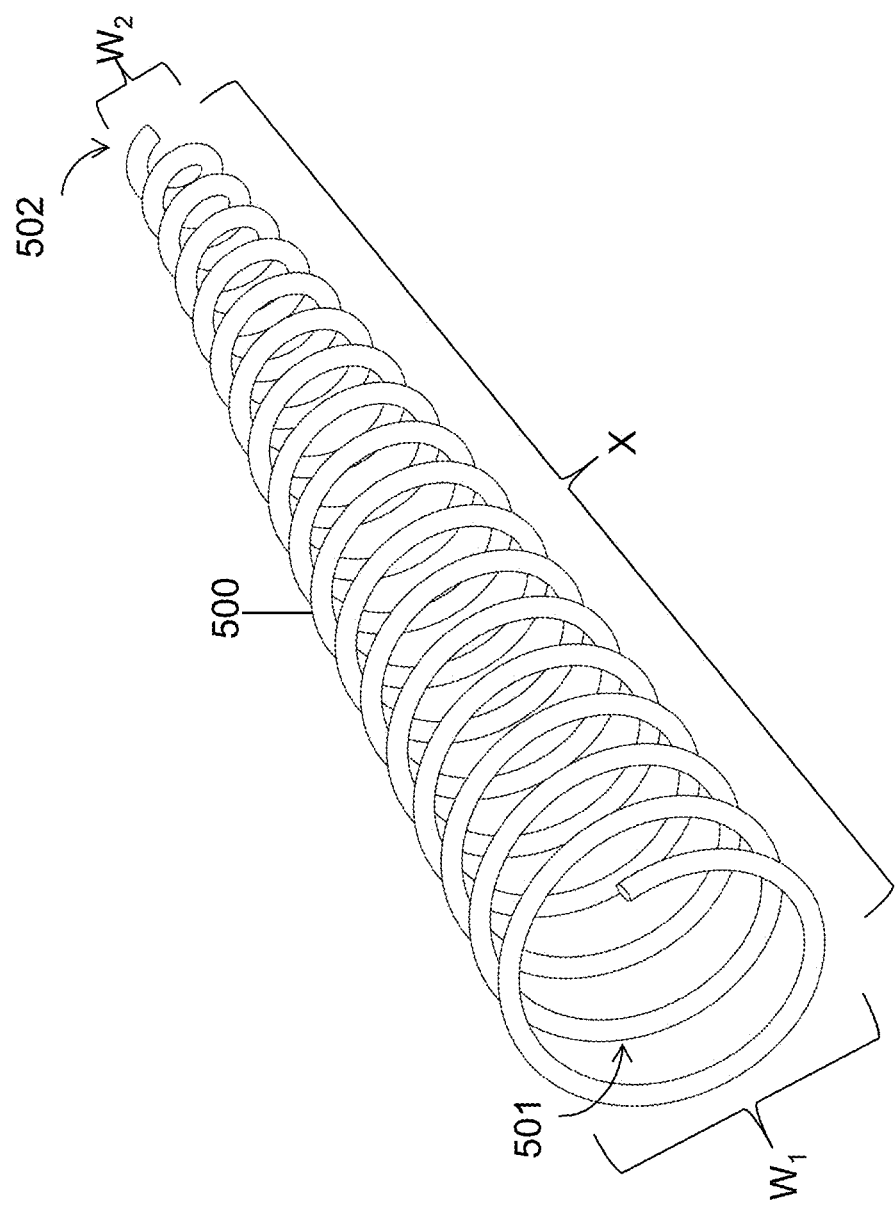
FIG. 5 is a perspective view of a tissue repair device, according to another embodiment, having a larger diameter at a first end of the device and a smaller diameter at an opposite second end of the device.

FIG. 5 shows a tissue repair device 500, according to another embodiment. The illustrated tissue repair device 500 may have a larger coil diameter $W_1$ on a first end 501 of the device 500 that can be varied by A and a smaller diameter $W_2$ at a second opposing end 502 that can be varied by B. This design may accommodate changes in a diameter of the tissue along its length X.

Figure 6:
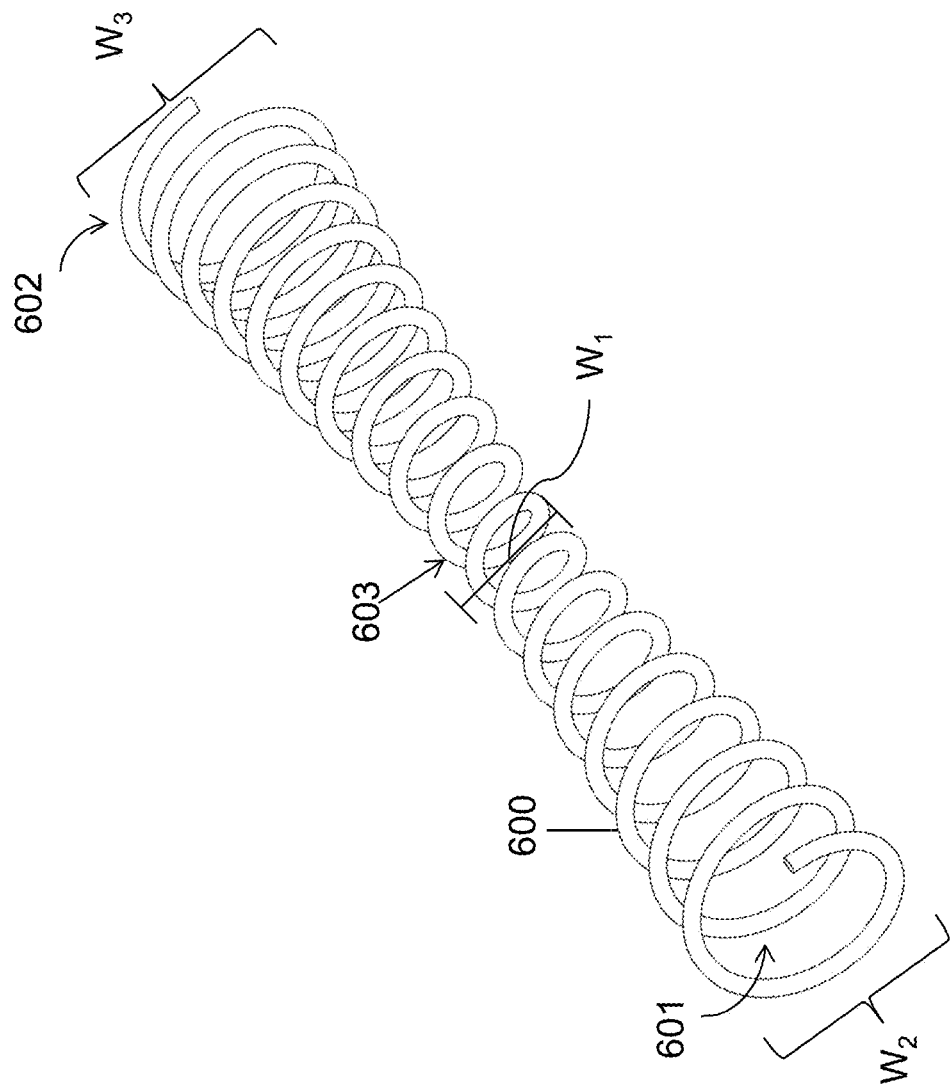
FIG. 6 is a perspective view of a tissue repair device, according to another embodiment, having a smaller diameter at a center portion and larger diameters towards each end.

FIG. 6 shows a tissue repair device 600, according to another embodiment. The illustrated tissue repair device 600 may have a smaller coil diameter $W_1$ towards a center portion 603 that can be varied by X and a larger coil diameter $W_2$ that can be varied by Y at a first end 601 and the same or different larger coil diameter $W_3$ that can be varied by Z at an opposing second end 602.

Figure 7:
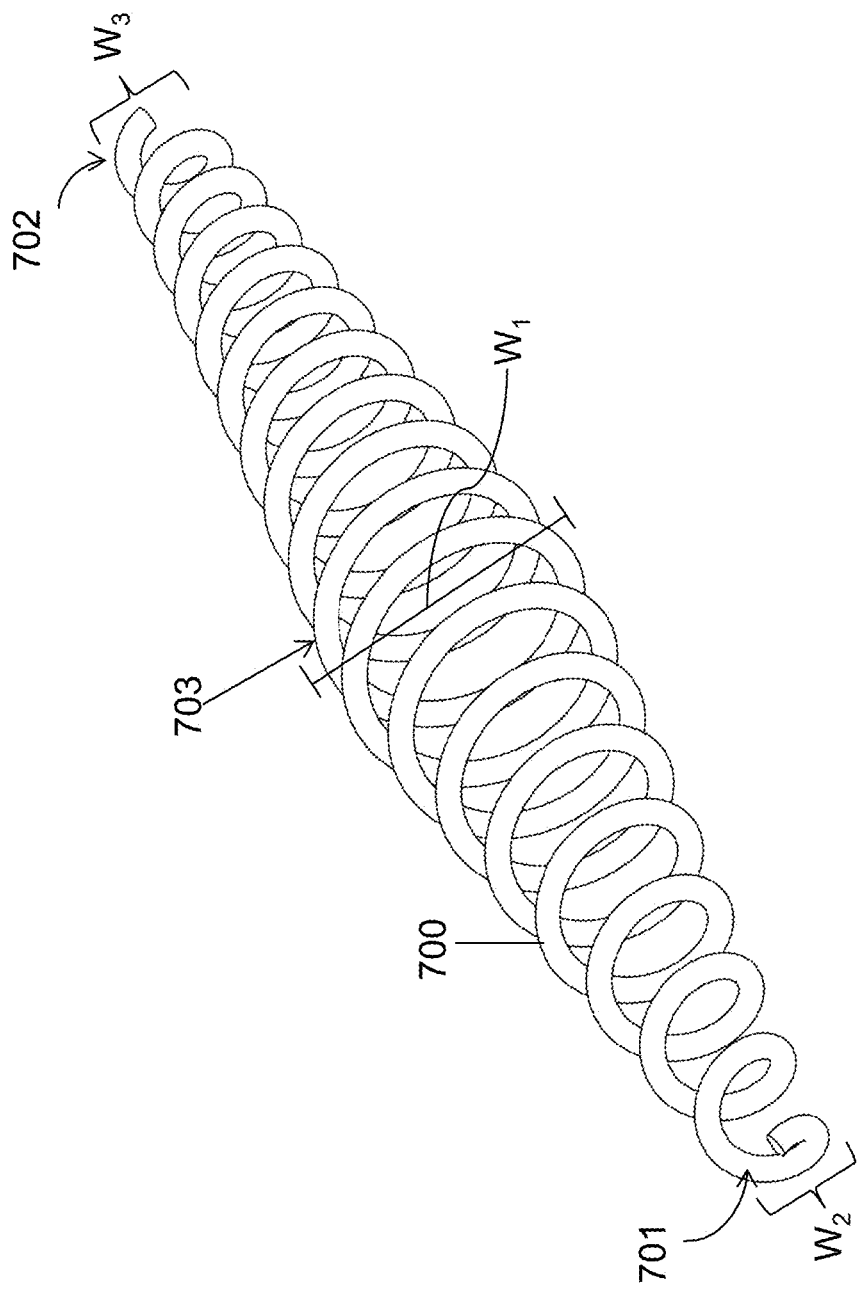
FIG. 7 is a perspective view of a tissue repair device, according to another embodiment, having a larger diameter at a center portion and smaller diameters towards each end.

FIG. 7 shows a tissue repair device 700, according to another embodiment. The illustrated tissue repair device may have a larger coil diameter $W_1$ that can be varied by X at a center portion 703 of the device 700 and a smaller coil diameter $W_2$ that can be varied by Y at a first end 701 and the same or different smaller coil diameter $W_3$ that can be varied by Z at the opposing second end 702.

Figure 8:
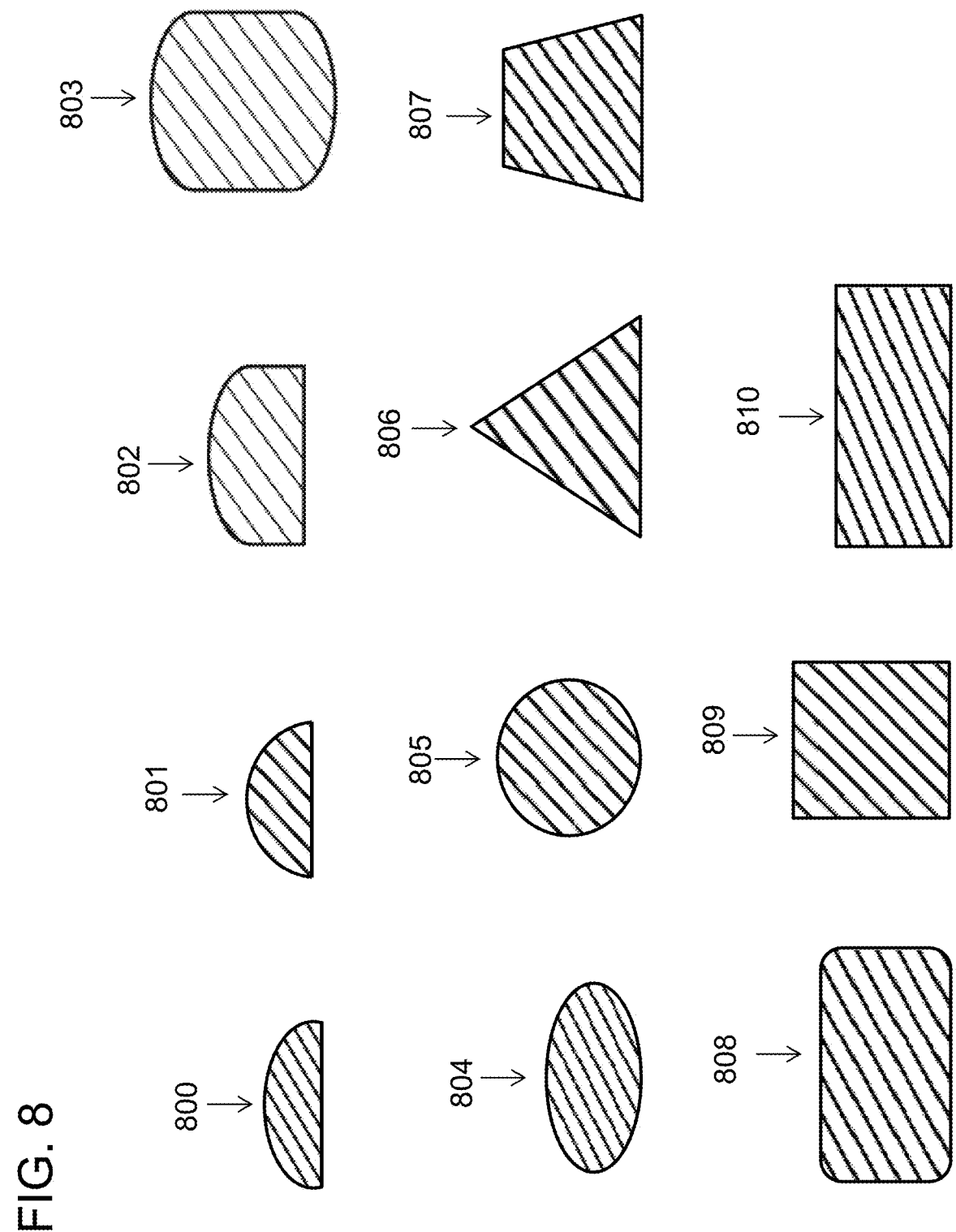
FIG. 8 shows various shaped transverse cross-sectional areas of a coil member of a tissue repair device.

FIG. 8 shows various shaped cross sectional areas 800-810 of a coil member (see coil member 103 of FIG. 1) of a tissue repair device. Varying cross sectional shapes can be used to maintain the tissue repair device in contact with the tissue and to enable the proper movement of the device within the body. The dimensions of the cross sectional areas 800-810 can be altered to best suit the implant situation. The various examples illustrated are merely representative, and are not in any way limiting of the scope of the present disclosure.

Figure 9:
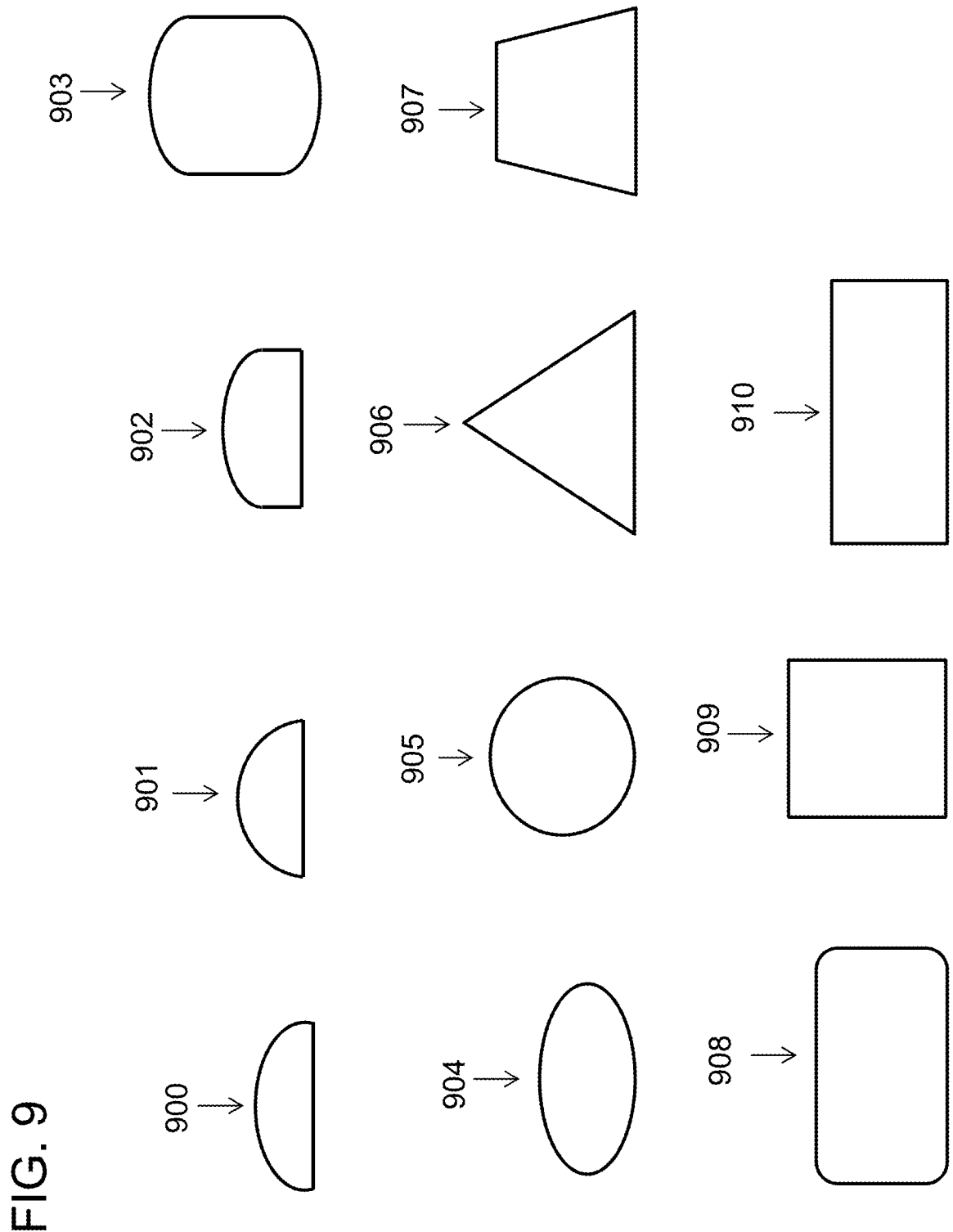
FIG. 9 shows transverse cross-sectional views of various tissue repair devices, illustrating varying shaped lumens of tissue repair devices.

FIG. 9 shows transverse cross sectional areas 900-910 of various tissue repair device, illustrating that varying shaped lumen may be defined by the tissue repair device and can be used to maintain the tissue repair device in contact with the tissue and to enable the proper movement of the device within the body. The dimensions of the cross sectional areas 900-910 can be altered to best suit the implant situation. The various examples illustrated are merely representative, and are not in any way limiting of the scope of the present disclosure.

Figure 10B:
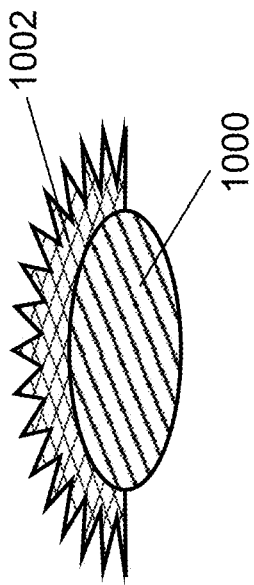
FIGS. 10A-10D are cross-sectional views of various embodiments of a coil member of a tissue repair device, showing the coil member with a macro or micro texture on all or part of a surface.
Figure 10D:
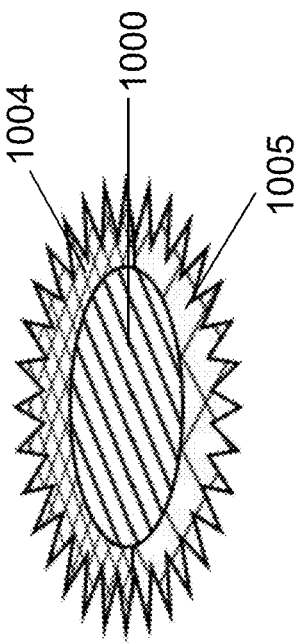
Figure 10A:
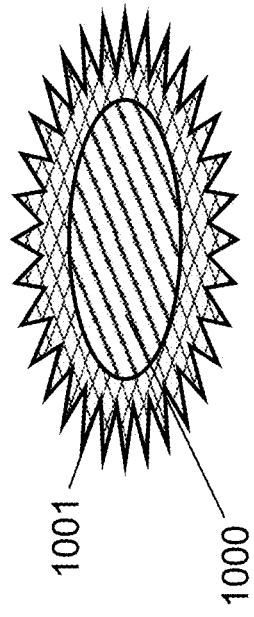
Figure 10C:
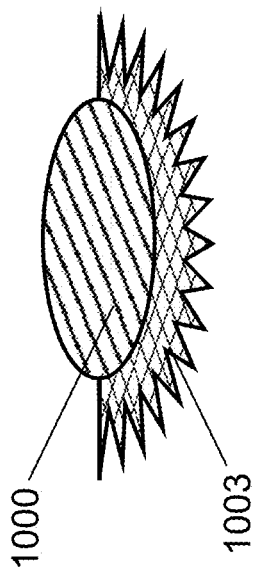

FIG. 10A-D shows example magnified cross sectional views of a coil member 1000, according to various embodiments, to illustrate that the coil member 1000 can be textured on all surfaces 1001, as shown in FIG. 10A. The texture may provide one of nano-, micro-, meso- and macro-textured surfaces on the coil member 1000. The coil member 1000 can have texture only along a top surface 1002 or outer surface 1002, as shown in FIG. 10B, thereby effect (e.g., engaging) the surrounding tissue and environment. The coil member 1000 can have texture only along the bottom surface 1003, or inner surface 1003, as seen in FIG. 10C, thereby effect (e.g., engaging) the elongate tissue to be repaired. FIG. 10D shows different texture along the top or outer surface 1004 and the bottom or inner surface 1005 of the coil member 1000. Textured surfaces can increase surface area, which may enable increased friction and thereby limit slipping of a device of along tissue to be repaired and/or along surrounding tissue. The surface texture may also increase or decrease tissue adhesion as appropriate. Surface texture can be used as appropriate to enhance, or even optimize functionality and ability to repair or support injured tissue. The coil member 1000 may also be smooth, or substantially free of surface texture, on all surfaces.

Figure 11A:
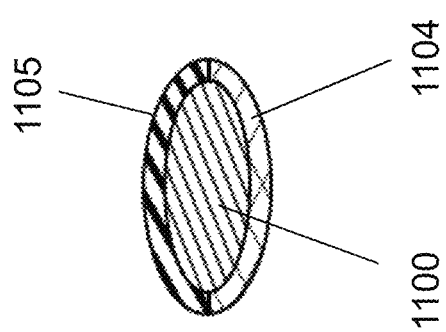
FIGS. 11A-11D are cross-sectional views of a coil member of various embodiments of a tissue repair device, showing the coil member with a coating on all or part of a surface.
Figure 11B:
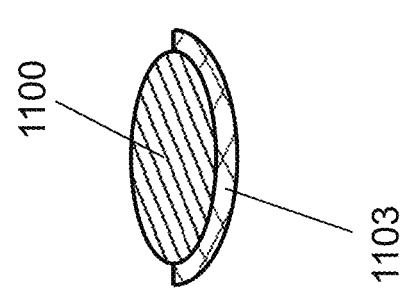
Figure 11C:
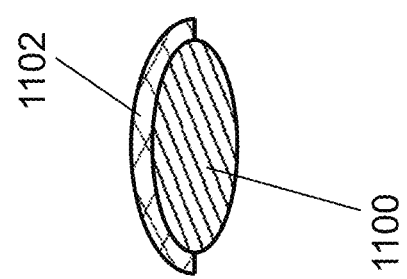
Figure 11D:
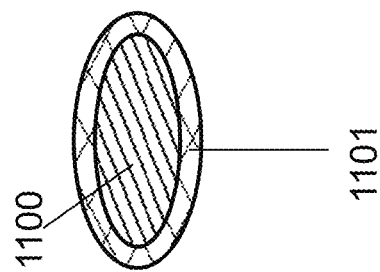

FIG. 11A shows a cross sectional area of the coil member 1100 illustrating the coil member 1000 can include a coating 1101 on all sides 1102. FIG. 11B shows the coil member 1100 with a coating 1102 only along the top or outer surface that affects the outside of the device or tissue surrounding the device. FIG. 11C shows the coil member 1100 with a coating 1103 only along a bottom or inner surface that affects the inside of the device adjacent to the tissue to be repaired. FIG. 11D shows the coil member 1100 with a coating 1105 along the top our outer surface 1105 and a different coating 1104 along the bottom or inner surface. The foregoing described coatings can comprise altered surface chemistry, chemical coatings, mineral coatings, biological coatings such as proteins, cells, sugars, lipids, etc., and cells such as stem cells, fibroblasts, chondrocytes, epithelial cells, endothelial cells, smooth muscle cells, macrophages, etc. These coatings can assist in cell adhesion, tissue regeneration, and preventing cell adhesion and tissue growth. Coatings can be used to optimize this device's functionality and ability to repair or support injured tissue.

In one embodiment, the coatings described above may be porous. A porous surface of the coiled member may promote cellular in-growth, which may further stabilize and ensure fixation of the tissue repair device relative to surrounding tissue. In another embodiment, the coiled member 1100 itself may be porous and the coating may reduce porosity where cellular in-growth may not be desired.

FIG. 12A shows a tissue repair device 1200, according to one embodiment. The tissue repair device 1200 is disposed around and engaging an elongate tissue 1202. In FIG. 12A, injured tissue 1203 is shown pressing up (or out) between the turns 1206 of the device 1200. If a diameter of the device 1200 is smaller than a diameter of the elongate tissue 1202, then portions of the injured tissue 1203 may press up (or out) between each turn 1206 of the device 1200. The buckling or pressing up (or out) of the portions of the tissue 1203 between each turn 1206 of the tissue repair device 1200 may create multiple catch points that may prevent the tissue 1202 and device 1200 from sliding relative to each other and/or past one another.

FIG. 12B shows the buckling or pressing up of tissue 1203 between each turn 1206 of the device 1200 during extension of the tissue repair device 1200 and elongate tissue 1202. In the case of ligaments or tendons that do not have vasculature, this construction and buckling may not limit or prevent diffusion of nutrients in the tissue. Also only slight buckling may be sufficient that may not greatly reduce the overall length of the tissue. If the tissue to be repaired is a vessel, such as a blood vessel with a hollow lumen, then the diameter of the device can be adjusted so that no buckling of the tissue will occur and the device may be used as a support.

Figure 13A:
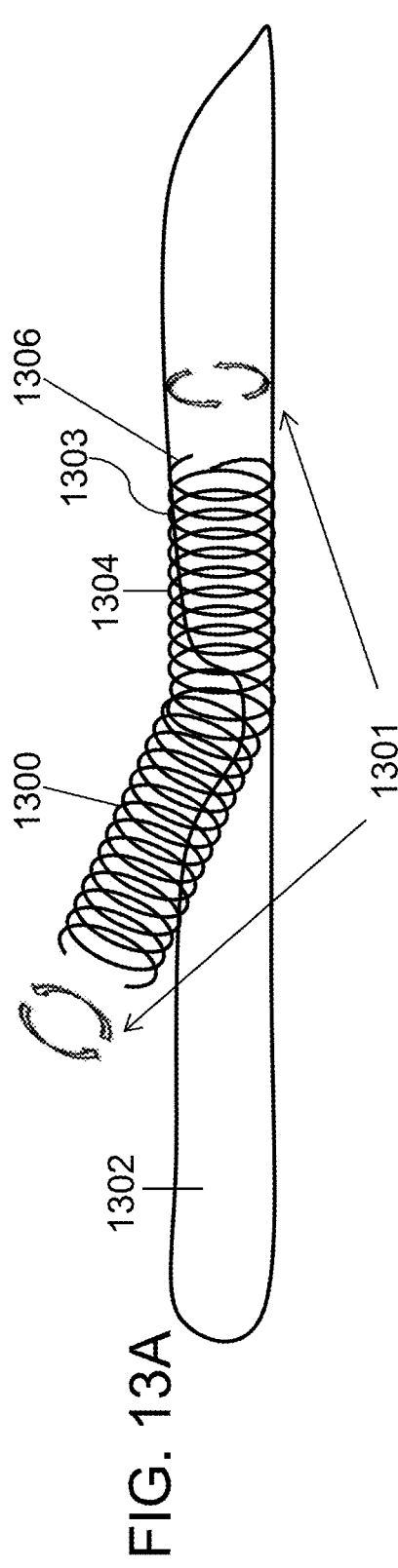
FIG. 13A illustrates deployment of a tissue repair device onto a partial or full tissue tear of an elongate tissue by twisting the coil onto the elongate tissue.
Figure 13B:
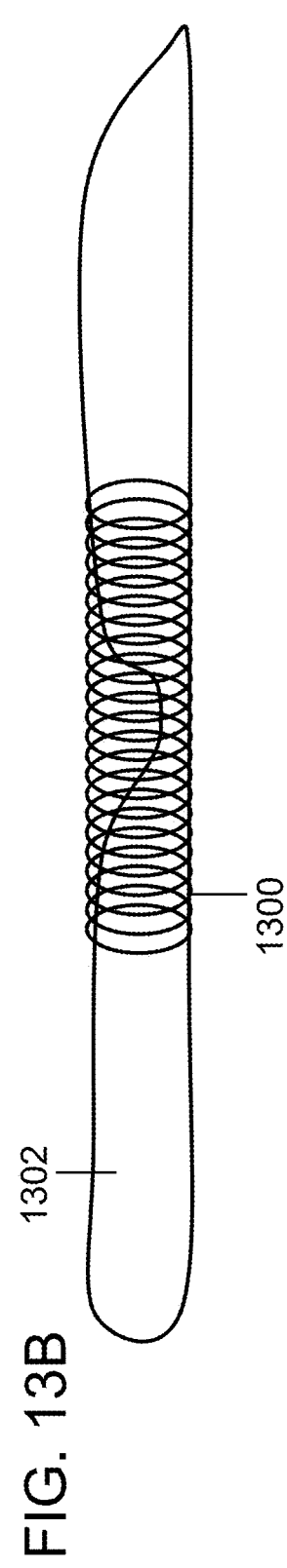
FIG. 13B illustrates the tissue repair device of FIG. 13A positioned in place on injured elongate tissue.
Figure 13C:
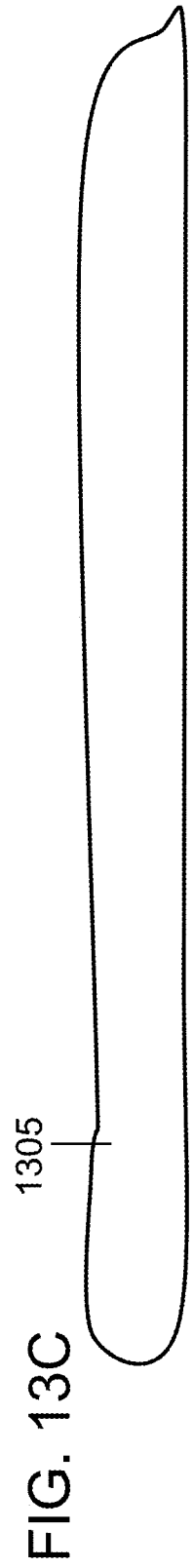
FIG. 13C illustrates the healed elongate tissue after the tissue repair device dissolves or is removed.

FIG. 13A Shows a method of deploying a device 1300 onto tissue 1302 that is partially or fully torn. An end 1306 of the coil member 1303 of the coil device 1300 can be placed on the tissue where there is an open end of the coil 1300. The device 1300 can be twisted in the direction shown by the arrows 1301 onto the tissue much like a key ring onto a key, twisting the device 1300, for example one turn 1304 at a time. FIG. 13B shows the device 1300 in place on the injured tissue 1302. An aspect of the disclosed embodiments, is that due to the coiled design, the embodiments can be placed onto tissues that are not completely lacerated, but can be twisted onto partially intact tissue. FIG. 13C shows healed tissue 1305, after the device 1300 dissolves or is removed.

As described above, a coil member 1303 of the tissue repair device 1300 may be formed of a biodegradable polymers and/or natural materials that can be broken down by the body after the injured tissue is sufficiently healed, allowing the native tissue to return to its normal state. The coil member 1303 can be infused with, or otherwise include nutrients, supplements, medicaments, sugars, growth factors, proteins, and/or hormones, which may promote and enhance healing of the elongate tissue. For example, as the biodegredable polymers and/or natural materials may include elements to promote tissue growth and/or healing that may be released as the biodegradeable polymers and/or natural materials are broken down by the body. Eventually the entire coil member 1303 may break down and/or be absorbed by the body, as shown in FIG. 13C.

Figure 14A:
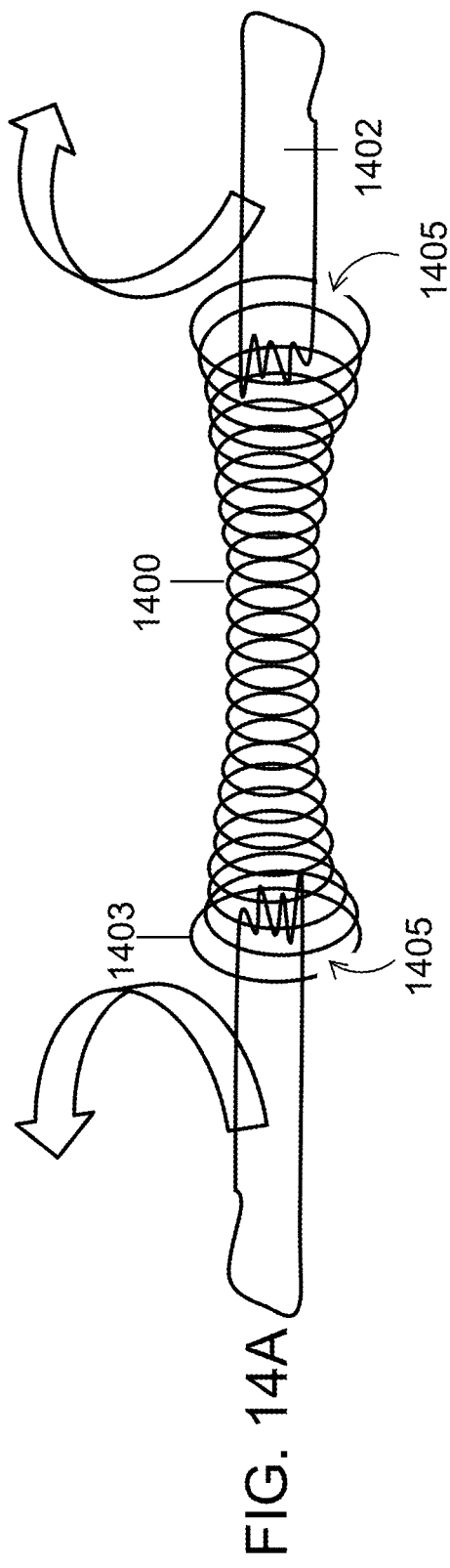
FIG. 14A illustrates deployment of a tissue repair device by reversing the twist in the coil, to increase a diameter of the turns of the coil to more easily place the injured elongate tissue within a lumen of the coil.
Figure 14B:
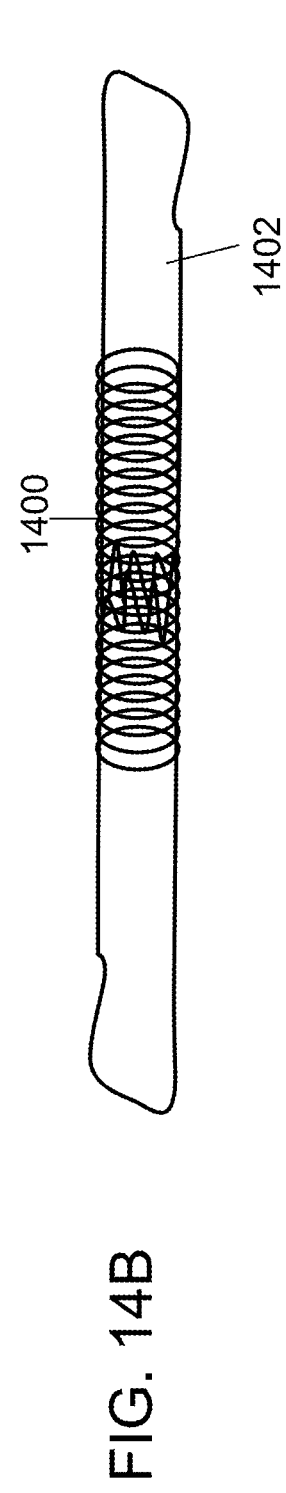
FIG. 14B illustrates the tissue repair device of FIG. 14A in place on the injured elongate tissue.
Figure 14C:
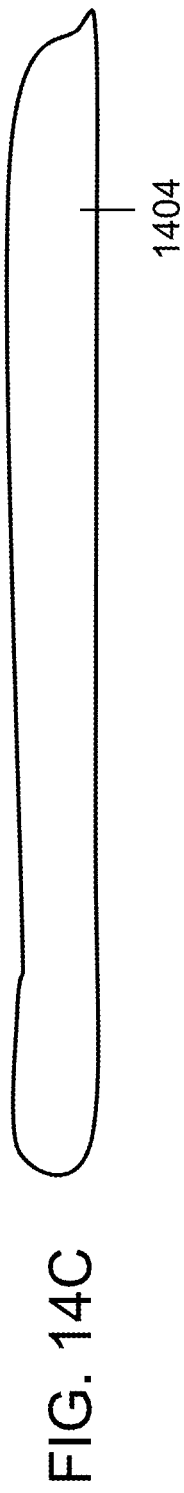
FIG. 14C illustrates the healed tissue after the tissue repair device dissolves or is removed.

FIG. 14A shows a method where a device 1400 can be twisted in the reverse direction of the coil member 1403 on either end in order to increase the diameter of the turns of the coil member 1403, enabling a larger space (lumen 1405) to insert the target injured elongate tissue 1402 to be repaired. FIG. 14A illustrate first and second free ends of torn elongate tissue 1402 being inserted into the lumen 1405 of the device 1400 such that the coil member 1403 can constrict around the free ends and draw and or maintain them together in close proximity. FIG. 14B shows the device 1400 in place on injured tissue 1402. The coil member 1403, and therefore the lumen 1405, of the device 1400 is constricted toward the relaxed state in engagement gripping the elongate tissue 1402. FIG. 14C shows healed tissue 1404 after the device 1400 dissolves or is removed.

FIGS. 15A and 15B show a method of threading sutures connected to tissue through a device 1500. FIG. 15A shows a pair of sutures 1504 that are sutured to each severed end of injured tissue 1502. The sutures 1504 can be threaded into and/or through a lumen 1505 of a tissue repair device 1500. FIG. 15B shows a method of threading the available end (or free end) of the sutures 1504 into and through a lumen the device 1500 and pulling the sutures 1504 through the device in order to pull the attached severed tissue 1502 into the device 1500. FIG. 15C shows severed tissue 1502 within and encircled by the device 1500.

Figure 16:
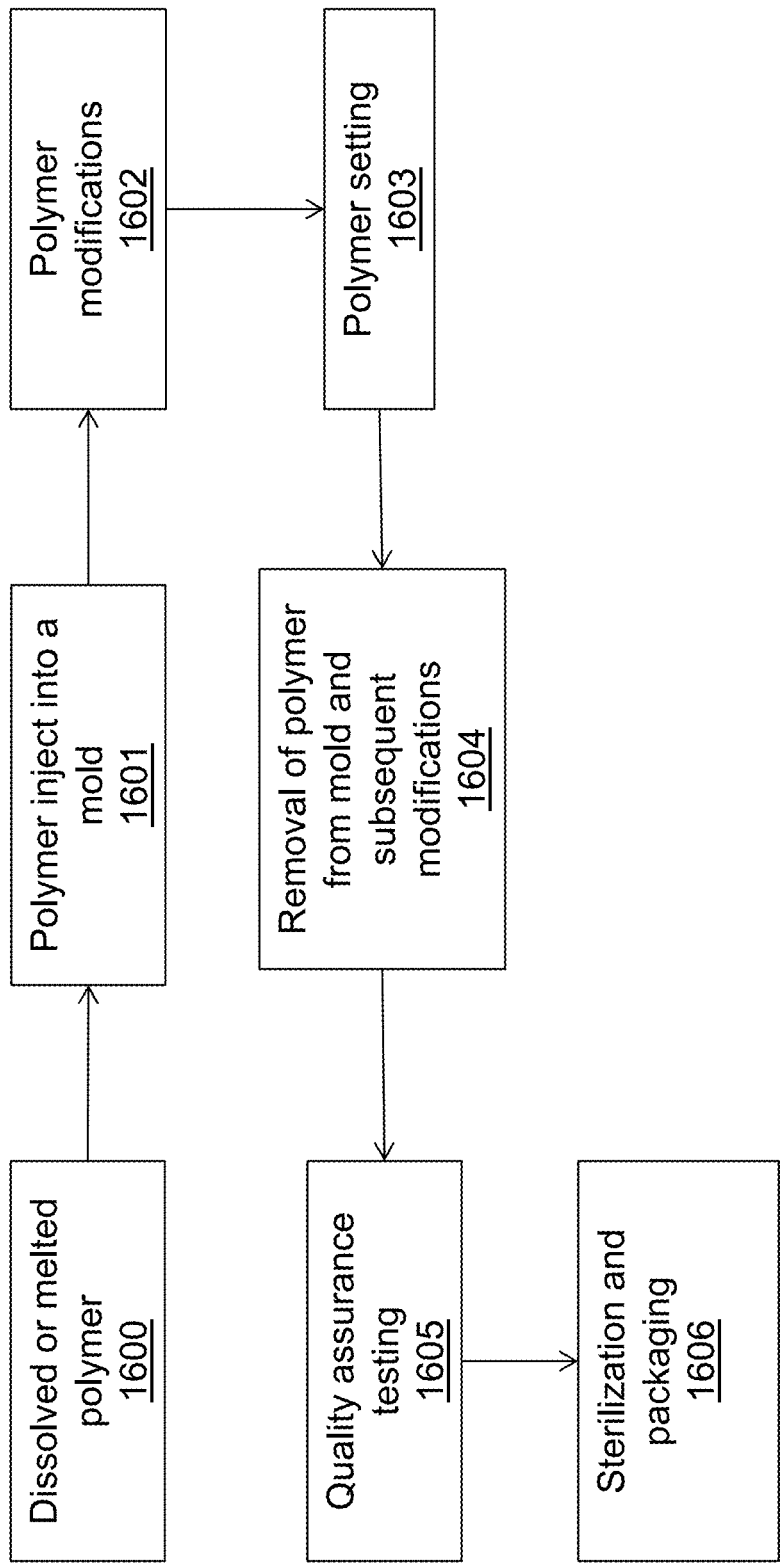
FIG. 16 is a flow diagram of a manufacturing process for producing a tissue repair device, according to one embodiment, by using an injection molding system.

FIG. 16 is a flow diagram of a manufacturing process for producing a device, according to one embodiment, by using an injection molding system. First a polymer (or other material of manufacture, e.g., metal) may be dissolved or melted 1600. Next the polymer is injected into a mold 1601. Next the polymer can be modified using physical or chemical processes 1602. Next the polymer is allowed to set 1603. Next the polymer can be removed from the mold and further modified using physical or chemical processes 1604. Next quality assurance testing can be performed on the device 1605. Lastly, sterilization and packaging may be performed 1606.

Figure 17:
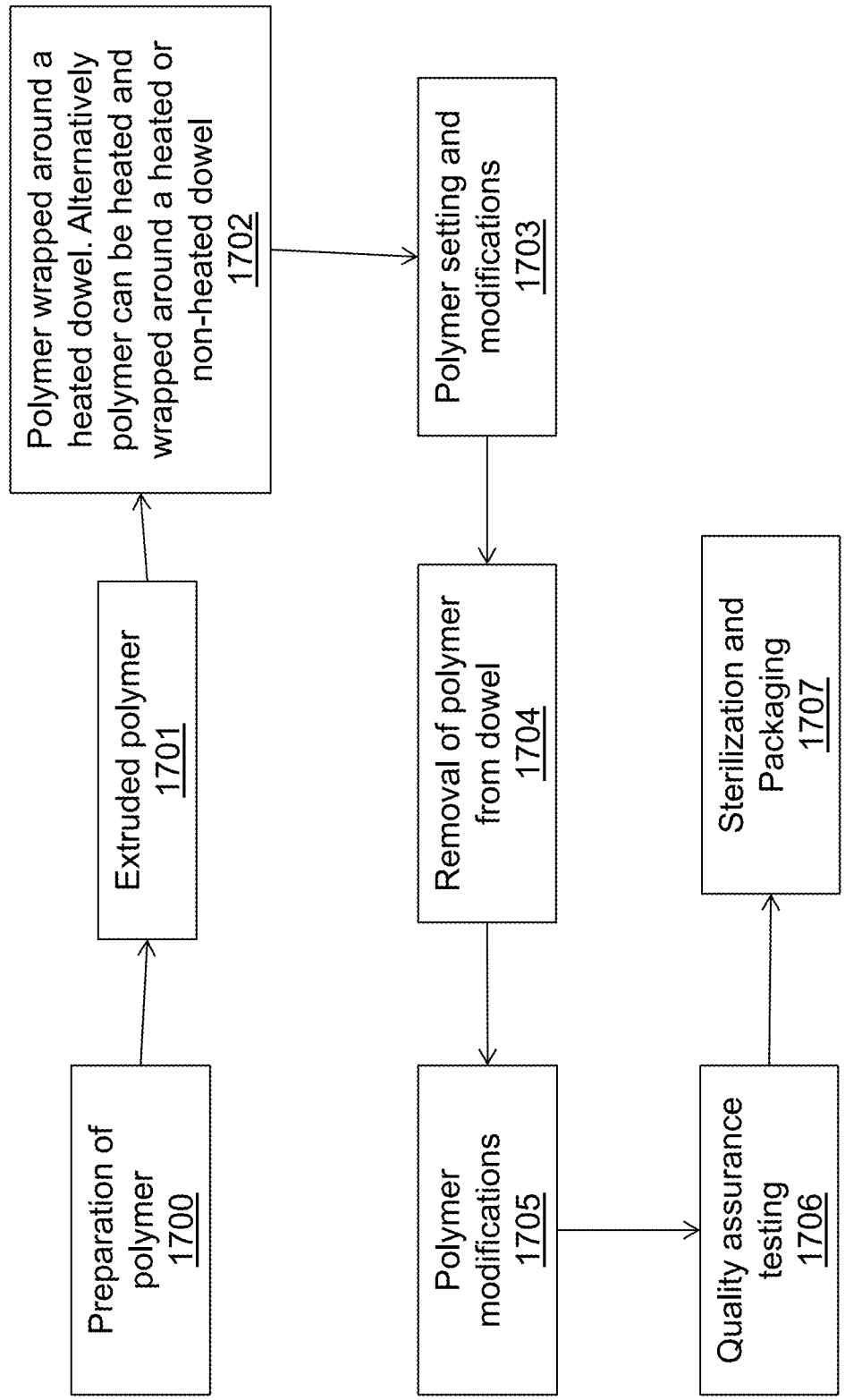
FIG. 17 is a flow diagram of a manufacturing process for producing a tissue repair device, according to one embodiment, by wrapping an extruded polymer around a heated dowel or heating the polymer and wrapping it around a dowel.

FIG. 17 is a flow diagram of a manufacturing process for producing a device, according to one embodiment of the present disclosure, by wrapping an extruded polymer around a heated dowel or heating the polymer and wrapping it around a heated or non-heated dowel. First the polymer is prepared 1700 by being dissolved, melted, etc. Next the polymer is extruded 1701. Next the polymer is wrapped around a heated dowel 1702. Alternatively the polymer can be heated and wrapped around a heated or non-heated dowel 1702. Next the polymer is allowed to set and may be modified using physical or chemical processes 1703. The polymer may be removed from the dowel 1704. The polymer may be further modified using physical or chemical processes 1705. Quality assurance testing may be performed on the device 1706. Sterilization and packaging may be performed 1707.

Figure 18:
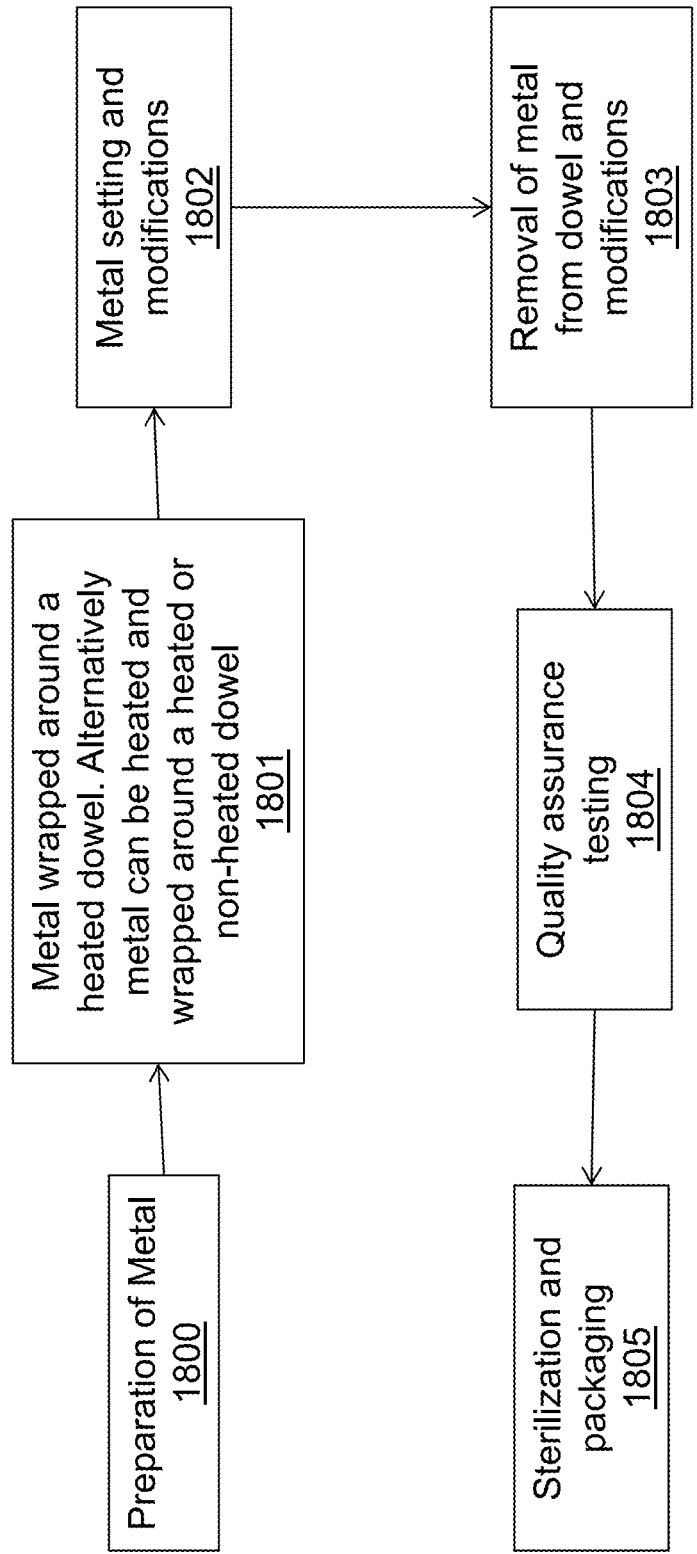
FIG. 18 is a flow diagram of a manufacturing process for producing a tissue repair device, according to one embodiment, by wrapping metal around a heated dowel or heating the metal and wrapping it around a dowel.

FIG. 18 is a flow diagram of a manufacturing process for producing a device, according to the present disclosure, by wrapping metal around a heated dowel or heating the metal and wrapping it around a heated or non-heated dowel. First the metal is prepared 1800. Next the metal is wrapped around a heated dowel 1801. Alternatively the metal can be heated and wrapped around a heated or non-heated dowel 1801. Next the metal is allowed to set and can be subsequently modified using physical or chemical processes 1802. Next the metal can be removed from the dowel and further modified using physical or chemical processes 1803. Next quality assurance testing can be performed on the device 1804. Lastly, sterilization and packaging may be performed 1805.

Additional embodiments include any suitable combination of the features depicted in the drawings. Accordingly, although a specific permutation may not be illustrated as a stand-alone embodiment in any of the drawings, all of the features are shown and described in the drawings such that the present drawings provide full support for these additional embodiments.

The disclosed embodiments may comprise a device with a center shape that can accommodate the shape of the tissue to be ligated or supported. These shapes include but are not limited to: circle, elliptical, square, rectangle, triangle trapezoid, or any combination of these shapes that may change shape along the length of the device. For example one end can begin as a circle cross section, but end as an ellipsoid cross section.

The disclosed embodiments may use the number and tightness of coils to control the grip onto the tissue The disclosed embodiments may use principles of friction and constriction to maintain contact with tissue.

The disclosed embodiments may comprise a coil member used to make a coil that can have various shaped cross-sectional areas including circle, elliptical, square, rectangle, triangle trapezoid, etc., or any combination of these shapes and where these shapes can change along the length of the coil member.

The disclosed embodiments may comprise a coil member that can be made of varying thicknesses of material that can vary along the length of the device.

The disclosed embodiments where the device comprises an elongate hollow coiled member of biocompatible, surgically implantable material. The member having a first and second end, with the device being open at both ends.

The disclosed embodiments may comprise a method for treating weakened, damaged, and partially or completely lacerated tissue, wherein this method comprises obtaining a tissue repair device and accessing injured tissue within the body.

One of the disclosed embodiments may be a method of manufacturing a tissue repair device, comprising: preparing a biocompatible material; forming the biocompatible material into a coil comprising a series of interconnected turns defining a lumen through the coil, the lumen being open at both ends and configured to receive and encircle an elongate tissue to be repaired, wherein the material in a hardened state is configured to allow the coil to be extendable to increase a distance between adjacent turns of the plurality of turns and increase a length of the coil and to decrease a diameter of one or more of the turns of the plurality of turns proportional to extension of the length to more tightly engage an elongate tissue disposed within the lumen to decrease tension at a wound site of the elongate tissue by distributing tension along a length of the coil; and allowing the biocompatible material to set.

The method of manufacture may further include texturing an inner surface of the coil to enhance engagement of the inner surface with tissue to be repaired and limit sliding of the tissue repair device relative to the tissue to be repaired.

The examples and embodiments disclosed herein are to be construed as merely illustrative and exemplary, and not a limitation of the scope of the present disclosure in any way. It will be understood to those having skill in the art that changes may be made to the details of the above-described embodiments without departing from the underlying principles of the disclosure herein. For example, any suitable combination of various embodiments, or the features thereof, is contemplated. For example, any of the devices disclosed herein can include features of other embodiments. The scope of the invention is therefore defined by the following claims and their equivalents.

What is claimed is:

1. A method of supporting tissue, the method comprising:
obtaining a tissue repair device comprising a coil formed by an elongate coil member of biocompatible material having a first end and a second end and configured in a spiral pattern to form a series of interconnected turns and to define a lumen through the coil member being open at both ends to receive, encircle, and engage target elongate tissue to be treated;
accessing within a body the target elongate tissue;
positioning the tissue repair device with the coil around the target elongate tissue, with the target elongate tissue disposed through the lumen with an inner surface of the series of interconnected turns engaging the target elongate tissue; and
attaching sutures to ends of the elongate tissue to be joined and passing a free end of the sutures that are not attached to elongate tissue through the tissue repair device in opposite directions and pulling the ends of the elongate tissue into the tissue repair device.

2. The method of claim 1, wherein supporting tissue comprises connecting together a first free end and a second free end of a torn elongate tissue, the method further comprising:
drawing together the first free end and the second free end of the torn elongate tissue to be connected, and wherein positioning the tissue repair device includes positioning the first and second free ends to be connected within the lumen with an inner surface of the series of interconnected turns engaging the target elongate tissue and maintaining the first free end and the second free end of the target elongate tissue in close proximity to each other.

3. The method of claim 1, wherein the coil is extendable from a relaxed state to an extended state and each turn of the series of interconnected turns has a first diameter when in the relaxed state and a second smaller diameter when in the extended state.

4. The method of claim 1, wherein the tissue repair device is configured such that tensile stress on the elongate tissue extends the coil to the extended state and thereby distributes tension resulting from the tensile stress along the target elongate tissue through a length of the coil.

5. The method of claim 1, wherein the tissue repair device is configured such that a first end can be mounted to a bone and a second end can encircle soft tissue and thereby relieve tension at a bone-soft tissue interface.

6. The method of claim 1, wherein positioning the tissue repair device comprises:
twisting the coil member in a direction opposite a direction of the spiral pattern to increase a diameter of one or more turns of the series of interconnected turns to allow positioning of the coil around the target elongate tissue, with an injured tissue disposed within the lumen of the tissue repair device and an inner surface of the series of interconnected turns engaging the target elongate tissue.

7. A method of supporting elongate tissue, the method comprising:
obtaining a tissue repair device comprising a coil formed by an elongate coil member of biocompatible material having a first end and a second end and configured in a spiral pattern to form a series of interconnected turns and to define a lumen through the coil member being open at both ends to receive, encircle, and engage target elongate tissue to be treated;
accessing within a body the target elongate tissue;
positioning the tissue repair device with the coil around the target elongate tissue by:
engaging a first interconnected turn of the series of interconnected turns of the coil member of the tissue repair device around the target elongate tissue; and
twisting the coil member of the tissue repair device onto the target elongate tissue to incrementally engage each interconnected turn of the series of interconnected turns of the coil member of the tissue repair device around the target elongate tissue to position the target elongate tissue through the lumen with an inner surface of the series of interconnected turns engaging the target elongate tissue.

8. The method of claim 7, wherein the coil is extendable from a relaxed state to an extended state and each turn of the series of interconnected turns has a first diameter when in the relaxed state and a second smaller diameter when in the extended state.

9. The method of claim 7, wherein the tissue repair device is configured such that tensile stress on the target elongate tissue extends the coil to the extended state and thereby distributes tension resulting from the tensile stress along the target elongate tissue through a length of the coil.

10. The method of claim 7, wherein the tissue repair device is configured such that a first end can be mounted to a bone and a second end can encircle soft tissue and thereby relieve tension at a bone-soft tissue interface.

11. The method of claim 7, wherein the target elongate tissue is sutured prior to twisting the coil member of the tissue repair device onto the target elongate tissue.

12. The method of claim 7, wherein the target elongate tissue comprises one of a tendon or a ligament.

13. A method of supporting a damaged tendon, comprising:
obtaining a tissue repair device comprising a coil formed by an elongate coil member of biocompatible material having a first end and a second end and configured in a spiral pattern to form a series of interconnected turns and to define a lumen through the coil member being open at both ends to receive, encircle, and engage a damaged tendon to be supported;
accessing within a body the damaged tendon to be supported; and
positioning the tissue repair device with the coil around the damaged tendon by:
engaging a first interconnected turn of the series of interconnected turns of the coil member of the tissue repair device around the damaged tendon; and
twisting the coil member of the tissue repair device onto the damaged tendon to incrementally engage each interconnected turn of the series of interconnected turns of the coil member of the tissue repair device around the damaged tendon to position the damaged tendon through the lumen with an inner surface of the series of interconnected turns engaging the damaged tendon.

14. The method of claim 13, wherein the coil is extendable from a relaxed state to an extended state and each turn of the series of interconnected turns has a first diameter when in the relaxed state and a second smaller diameter when in the extended state.

15. The method of claim 13, wherein the tissue repair device is configured such that tensile stress on the damaged tendon extends the coil to the extended state and thereby distributes tension resulting from the tensile stress along the damaged tendon through a length of the coil.

16. The method of claim 13, wherein the tissue repair device is configured such that a first end can be mounted to a bone and a second end can encircle soft tissue and thereby relieve tension at a bone-soft tissue interface.

17. The method of claim 13, wherein the damaged tendon is sutured prior to twisting the coil member of the tissue repair device onto the damaged tendon.

\* \* \* \* \*